US010835576B2

(12) United States Patent
Padliya et al.

(10) Patent No.: US 10,835,576 B2
(45) **Date of Patent: *Nov. 17, 2020**

(54) METHOD OF OBTAINING EFFECTIVE AMOUNTS OF AVIAN FOLLISTATIN

(71) Applicant: MYOS RENS TECHNOLOGY INC., Cedar Knolls, NJ (US)

(72) Inventors: Neerav Padliya, South Grafton, MA (US); Robert J. Hariri, Benardsville, NJ (US); Carlon Colker, Stamford, CT (US)

(73) Assignee: MYOS RENS TECHNOLOGY INC., Cedar Knolls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/557,419

(22) Filed: Dec. 1, 2014

(65) Prior Publication Data

US 2015/0238566 A1 Aug. 27, 2015

Related U.S. Application Data

(63) Continuation-in-part of application No. 11/750,128, filed on May 17, 2007, now abandoned.

(60) Provisional application No. 61/910,277, filed on Nov. 29, 2013, provisional application No. 60/801,266, filed on May 18, 2006.

(51) Int. Cl.
*A61K 38/17* (2006.01)
*A61K 35/57* (2015.01)
*A23L 33/17* (2016.01)
*A23L 15/00* (2016.01)

(52) U.S. Cl.
CPC .......... *A61K 38/1703* (2013.01); *A23L 15/00* (2016.08); *A23L 33/17* (2016.08); *A61K 35/57* (2013.01); *A23V 2002/00* (2013.01)

(58) Field of Classification Search
CPC ... A61P 21/00; A61P 21/06; A23V 2250/5428
See application file for complete search history.

(56) References Cited

U.S. PATENT DOCUMENTS

| | | | | |
|---|---|---|---|---|
| 3,607,304 | A | 9/1971 | Levin | |
| 3,930,054 | A | 12/1975 | Liot et al. | |
| 5,641,517 | A * | 6/1997 | Eskeland et al. | 424/520 |
| 6,686,198 | B1 | 2/2004 | Melton | |
| 6,921,644 | B2 | 7/2005 | Duan | |
| 2007/0275036 | A1 * | 11/2007 | Green, III et al. | 424/439 |

FOREIGN PATENT DOCUMENTS

| | | | |
|---|---|---|---|
| FR | 2811898 | | 7/2000 |
| WO | WO-1998-55143 | A1 | 12/1998 |

OTHER PUBLICATIONS

Wagner “Muscle regeneration through myostatin inhibition” Curr Opin Rheumatol 17:720-724, 2005.*
Hiperbaric “What is High Pressure Processing” 4 pgs, copyright 2012.*
Encyclopedia Britannica Online “Egg” acessed May 25, 2018, article published Jul. 26, 1999, 4pgs.*
The Hammersmith Hospitals NHS Trust “Muscular Dystrophy Campaign: Healthy Eating for Children” 5pgs published Dec. 2004.*
Appel et al. “Meals for Easy Swallowing” 113 pgs, 2005.*
Haidet et al. “Long-term enhancement of skeletal muscle mass and strength by single gene administration of myostatin inhibitors” PNAS Mar. 18, 2008 vol. 105 No. 11, 4318-4322 (Year: 2008).*
Sepulveda et al. “Evaluation of follistatin as a therapeutic in models of skeletal muscle atrophy associated with denervation and tenotomy” Scientific Reports, vol. 5, Article 17535, Dec. 11, 2015/online, 11pgs (Year: 2015).*
Sharp et al. “The effects of a myostatin inhibitor on lean body mass, strength, and power in resistance trained males” Journal of the International Society of Sports Nutrition 2014, 11(Suppl 1):P42 (Year: 2014).*
Derwent Abstract for FR2811898, 2002 Derwent, Derwent Accession No. 2002-149755, pp. 1-4.
Case No. 308CV01654AWT Complaint and Jury Demand date Oct. 31, 2008.
Amthor H., et al “Follistatin regulates bone morphogenic protein-7 (BMP-7) activity to stimulate embryonic muscle growth,” Dev, Biol. 243(1):115-127(2002).
Amthor, H. et al., “The expression and regulation of follistatin and a follistatin-like gene during avian somite compartimentalization and myogenesis,” Dev. Biol. 187(2):343-362(1996).
Asashima, M. et al., “The vegetalizing factor from chicken embryos: its EDF (activin A)-like activity,” Mechanisms of Development 34(2-3):135-141(1991).
Belecky-Adams, T.L., et al., “Activin family members in the developing chick retina:expresson patterns, protein distribution, and in vitro effects,” Dev. Biol. 210(1):107-123(1999).
Chapman, S.C. et al, “Analysis of spatial and temporal gene expression patterns in blastula and gastrula stage chick embryos,” Dev. Biol.245(1):187-199(2002).

(Continued)

*Primary Examiner* — Thane Underdahl
(74) *Attorney, Agent, or Firm* — Licata & Tyrrell P.C.

(57) ABSTRACT

Embodiments of the present invention are generally related to methods of obtaining effective amount of avian follistatin. More specifically, embodiments of the present invention relate to products comprising avian follistatin, and methods of optimizing the same based on avian follistatin concentrations utilized during the manufacturing process. In one embodiment of the present invention, a method of creating a consumable product for treatment of a muscle degenerating disease having avian follistatin comprises selecting an avian egg based upon a desired threshold of avian follistatin concentration therein; extracting material from the avian egg, the material comprising avian follistatin; and processing the material with one or more excipients to yield the consumable product.

1 Claim, 4 Drawing Sheets

(56) References Cited

OTHER PUBLICATIONS

Colker, C. et al., "Randomized Blind Comparison of Follistatin in Standard Store-Bought Unfertilized Chicken Eggs Versus Standard Store-Bought Fertile Eggs," J. Am. College Nutrition 25(5):Poster Presentations: Abstract 65 (Oct. 2006).

Connolly, D.J. et al., "Effects of follistatin and BMP4 proteins on early dorso-ventral patterning in check," Intl. J. dev. Biol. 44(1):129-140(2000).

Connolly, D.J., et al., "Cloning, sequencing and expressional analysis of the chick homologue of follistatin," Dev. Genetics 17(1):65-77 (1995).

Case No. 308CV01654AWT Plaintiffs' Application for Temporary Restraining Order and Motion for Preliminary Injunction dated Dec. 30, 2008.

Kocamis. et al., "The ontogeny of myostatin, follistatin and activin-B mRNA expression during chicken embryonic development," Growth, Development & Aging, 1999 Winter;63(4):143-50.

Levin, "the roles of activin and follistatin signalling in chick gastrulation," Intl. J. Dev. Biol. 42(4):553-559 (1998).

Link, N.R., "Development of the avian iris and ciliary body: the role of activin and follistatin in coordinationof the smooth-to-striated muscle transition," Dev. Biol. 199(2):226-234(1998).

Link, B.a. et al., "Opposing effects of activin A and follistatin on developing skeletal muscle cells," Exp. Cell Research 233(2):350-362 (1997).

Patel, K. et al., "The role of long range, local and direct signalling molecules during chick feather bud development involving the BMPs, follistatin and the Eph receptor tyrosine kinase Eph-A4," Mechanisms of Development 86 (1-2):51-62 (1999).

Davis, C. and Reeves, R., "High value opportunities from the chicken egg," Rural Industries Research and Development Corporation Aug. 2002.

Wang, Y. et al., "Fatty Acid Determination in Chicken Egg Yolk: A Comparsion of Different Methods," Poultry Science 79:1168-1171 (2000).

Amthor et al., "Follistatin complexes Myostatin and antagonists Myostatin-mediated inhibition of myogenesis," Dev. Biol. 270:19-30 (2004).

Colker, C., "Absorption profile and hormonal influences of fertilized egg yolk ingestion in the human," J. AM. College Nutrition 25(5):Need Page Nos. (2006).

Lee, S.J., et al., Regulation of Myostatin activity and muscle growth, PNAS USA 98:9306-9311 (2001).

Patel et al., "The function of Myostatin and strategies of Myostatin blockade-new hope for therapies aimed at promoting growth of skeletal muscle," Neuromuscular Disorders 15:117-126(2005).

* cited by examiner

The Influence of Fertility Status on the Concentration of Follistatin in the Chicken Egg

| Section of the Egg | Unfertile (ng/g) | Fertile (ng/g) |
|---|---|---|
| Egg White | 61.3 (n =5) | 54.3 (n=5) |
| Egg Yolk & Chalaza Homogenate | 17.8 (n =5) | 15.6 (n=5) |

All 20 eggs analyzed were brown eggs obtained from a crossbreed of Rhode Island Red and Leghorn Chickens (Goffle Road Poultry Farm, Wyckoff, NJ).

Figure 1

Concentration of Follistatin in Different Compartments of Chicken Egg

| Section of the Egg | Follistatin Concentration (ng/g) |
|---|---|
| Chalaza | 32.5 ng/g (n = 10) |
| Yolk | 0 ng/g (n = 2) |
| Egg White | 15.6 ng/g (n = 2) |

Eggs were purchased from Foodtown (Cedar Knolls, NJ) and were obtained from Puglisi Farms (Howell, NJ). Averages reported above were calculated using an equal number of white and brown eggs.

Figure 2

Concentration of Follistatin Measured In White and Brown Chicken Eggs

| Section of the Egg | White Egg (ng/g) | Brown Egg (ng/g) |
| --- | --- | --- |
| Chalaza | 19.6 (n=1) | 45.3 (n=1) |
| Yolk | 0 (n=1) | 0 (n=1) |
| White | 16.0 (n=1) | 15.1 (n=1) |

Eggs were purchased from Foodtown (Cedar Knolls, NJ) and were obtained from Puglisi Farms (Howell, NJ). Averages reported above were calculated using an equal number of white and brown eggs.

Figure 3

Concentration of Follistatin in Egg White: Impact of Chicken Breed

| Type of Chicken | Follistatin Concentration (ng/g) |
| --- | --- |
| Goffle Road Farm (Wyckoff, NJ) | 61.3 (n=5) |
| Puglisi Farms (Howell, NJ) | 15.6 (n=2) |

Figure 4

METHOD OF OBTAINING EFFECTIVE AMOUNTS OF AVIAN FOLLISTATIN

CROSS-REFERENCE TO RELATED APPLICATIONS

This application is a continuation-in-part of U.S. patent application Ser. No. 11/750,128, filed May 17, 2007, entitled "Avian Follistatin Product," which claims priority to U.S. Provisional Patent Application Ser. No. 60/801,266, filed May 18, 2006, the disclosures of which are incorporated herein by reference in their entireties. This application also claims priority to U.S. Provisional Patent Application Ser. No. 61/910,277, filed Nov. 29, 2013, the disclosure of which is also incorporated herein by reference in its entirety.

BACKGROUND

Field of the Invention

Embodiments of the present invention are generally related to methods of obtaining effective amount of avian follistatin. More specifically, embodiments of the present invention relate to products comprising avian follistatin, and methods of optimizing the same based on avian follistatin concentrations utilized during the manufacturing process.

Description of the Related Art

Wasting of skeletal muscle is a serious health condition that accompanies many conditions, diseases or disorders. Wasting of skeletal muscle also accompanies ageing. One of the most devastating but least-discussed aspects of age-related decline is the onset of frailty, i.e., the progressive loss of robustness in multiple tissues and organ systems. On the other side of the scale, many athletes benefit from an increase in muscle mass. In either instance, there is a need for a method to create a product or products which can assist with the growth and slow the degeneration of muscle tissue.

SUMMARY

Embodiments of the present invention are generally related to methods of obtaining effective amount of avian follistatin. More specifically, embodiments of the present invention relate to products comprising avian follistatin, and methods of optimizing the same based on avian follistatin concentrations utilized during the manufacturing process.

In one embodiment of the present invention, a method of creating a consumable product for treatment of a muscle degenerating disease having avian follistatin comprises selecting an avian egg based upon a desired threshold of avian follistatin concentration therein; extracting material from the avian egg, the material comprising avian follistatin; and processing the material with one or more excipients to yield the consumable product.

BRIEF DESCRIPTION OF THE DRAWINGS

So the manner in which the above recited features of the present invention can be understood in detail, a more particular description of embodiments of the present invention, briefly summarized above, may be had by reference to embodiments, which are illustrated in the appended drawings. It is to be noted, however, the appended drawings illustrate only typical embodiments of embodiments encompassed within the scope of the present invention, and, therefore, are not to be considered limiting, for the present invention may admit to other equally effective embodiments, wherein:

FIGS. 1-4 depict tables showing an exemplary embodiment of product testing on multiple egg sources, parts of the egg, and fertilization status in accordance with an embodiment of the present invention;

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning may). Similarly, the words "include", "including", and "includes" mean including but not limited to. To facilitate understanding, like reference numerals have been used, where possible, to designate like elements common to the figures.

DETAILED DESCRIPTION

It is understood that the embodiments of the present invention are not limited to the particular methodologies, protocols and the like, described herein as they may vary. It is also to be understood the terminology used herein is used for the purpose of describing particular embodiments only and not intended to limit the scope of the present invention. Unless defined otherwise, all technical and scientific terms used herein have the same meaning as commonly understood by one of ordinary skilled in the art to which this invention belongs.

The protein known as avian follistatin, and in particular, chicken follistatin, has been identified as a very beneficial protein for human consumption as it pertains to the health of lean muscle tissue. Such benefits are described in part in commonly owned Untied States Patent Application Publication No. 2007/0275036, the disclosure of which is incorporated herein by reference in its entirety (hereinafter "Green Application").

As disclosed in the Green Application, one embodiment of an avian follistatin product may be derived by extracting follistatin from the membrane of a fertilized chicken egg. In such an embodiment, a product may be created which comprises a particular concentration of follistatin (measured in ng/g) which has been found to be highly advantageous for many individuals in the sports nutrition space. In short, for the target market of a commercial embodiment of one of the embodiments disclosed by Green has been identified as optimal for the product disclosed in the Green Application as derived from the concentrations of avian follistatin found in the membrane of fertilized chicken eggs.

However, in accordance with further embodiments of the present invention, other target markets have been found to benefit from alternative concentrations of avian follistatin. In accordance with one embodiment of the present invention, such concentration of avian follistatin may be modified during the manufacturing process through filtering processes, or the like. In further embodiments, however, selection of egg type, source, fertilization status, and the like, can have a significant impact on the concentrations of avian follistatin therein. Moreover, in many embodiments, selection of part of the egg used for the source of avian follistatin is found to have a substantial impact on the resulting concentrations. As such, by tracking the impact of each of the characteristics of an egg and measuring avian follistatin concentrations therein, tables may be created such that optimized products may be created from egg source.

FIGS. 1-4 depict tables showing an exemplary embodiment of product testing on multiple egg sources, parts of the egg, and fertilization status. As shown in the tables, a substantial difference in avian follistatin concentration was discovered across each field.

Accordingly, in manufacturing products in accordance with the embodiments of the present invention, and those taught in the Green Application, the selection process set forth herein may be utilized to optimize such products for an intended target market.

While the foregoing is directed to embodiments of the present invention, other and further embodiments of the invention may be devised without departing from the basic scope thereof. It is also understood that various embodiments described herein may be utilized in combination with any other embodiment described, without departing from the scope contained herein.

What is claimed is:

1. A method of increasing muscle mass in an individual with a muscle degenerating disease associated with wasting of skeletal muscle, said method comprising:

making a drinkable product comprising avian follistatin and a liquid; and administering the drinkable product orally to the individual in an amount effective to provide an increase in muscle mass to the individual.

* * * * *